(12) United States Patent
Houcek et al.

(10) Patent No.: US 11,533,573 B2
(45) Date of Patent: Dec. 20, 2022

(54) RECEIVER HOUSING WITH INTEGRATED SENSORS FOR HEARING DEVICE

(71) Applicant: Knowles Electronics, LLC, Itasca, IL (US)

(72) Inventors: Earl E. Houcek, Carol Stream, IL (US); Matthew Manley, Crystal Lake, IL (US); Daryl Barry, Wilmette, IL (US); Yahui Zhang, Schaumburg, IL (US); Steve Kearey, Carpentersville, IL (US)

(73) Assignee: KNOWLES ELECTRONICS, LLC, Itasca, IL (US)

( * ) Notice: Subject to any disclaimer, the term of this patent is extended or adjusted under 35 U.S.C. 154(b) by 0 days.

(21) Appl. No.: 16/694,293

(22) Filed: Nov. 25, 2019

(65) Prior Publication Data

US 2020/0213787 A1 Jul. 2, 2020

Related U.S. Application Data

(60) Provisional application No. 62/786,992, filed on Dec. 31, 2018.

(51) Int. Cl.
*H04R 25/00* (2006.01)
*A61B 5/00* (2006.01)
*H04R 1/10* (2006.01)

(52) U.S. Cl.
CPC ......... *H04R 25/652* (2013.01); *A61B 5/6817* (2013.01); *H04R 1/1033* (2013.01);
(Continued)

(58) Field of Classification Search
CPC .............. H04R 2225/41; H04R 1/1016; A63B 2230/04; A63B 2230/08
(Continued)

(56) References Cited

U.S. PATENT DOCUMENTS 7,822,218 B2 * 10/2010 Van Halteren ......... H04R 11/02
381/322
8,254,608 B2 8/2012 De Finis
(Continued)

FOREIGN PATENT DOCUMENTS

DE 202018107057 U1 12/2018
EP 2040343 A1 3/2009
WO 2007/140403 A2 12/2007

OTHER PUBLICATIONS

WIDEX; Audiological Bulletin No. 50, Customising receiver ear-sets for Passion hearing aids and removing the battery drawer to connect programming cables; Mar. 13, 2008.
(Continued)

*Primary Examiner* — George C Monikang

(57) ABSTRACT

A hearing device and subassembly therefor includes a sleeve member configured for at least partial insertion into a user's ear canal, the sleeve member defining a cavity that receives and retains at least a portion of a sound-producing electroacoustic transducer. The sleeve member includes a cable interface, wherein an electrical interface of a sound-producing electroacoustic transducer received in the cavity is accessible via the cable interface. The device also includes on or more sensors integrated with the sleeve member and positioned to sense a biomarker or other condition when the sleeve member is at least partially inserted into the user's ear canal. The hearing device includes conductive traces integrated with the sleeve member, where at least one conductive trace is electrically connected to the sensor and electrically connectable via the cable interface.

19 Claims, 6 Drawing Sheets

(52) U.S. Cl.
CPC ......... *H04R 1/1075* (2013.01); *H04R 1/1091* (2013.01); *H04R 25/48* (2013.01); *H04R 25/556* (2013.01)

(58) Field of Classification Search
USPC .................................. 381/312, 328, 74, 322
See application file for complete search history.

(56) References Cited

U.S. PATENT DOCUMENTS

| | | | |
|---|---|---|---|
| 2002/0102004 A1* | 8/2002 | Minervini | B81B 7/0064 381/175 |
| 2008/0205679 A1 | 8/2008 | Darbut et al. | |
| 2011/0051966 A1* | 3/2011 | De Finis | H04R 25/658 381/322 |
| 2015/0023539 A1* | 1/2015 | Bauman | H04R 25/554 29/601 |
| 2016/0199001 A1 | 7/2016 | Lee et al. | |

OTHER PUBLICATIONS

European Patent Office; International Search Report and Written Opinion; International Application No. PCT/US/2019/064258; dated Feb. 12, 2020.

* cited by examiner

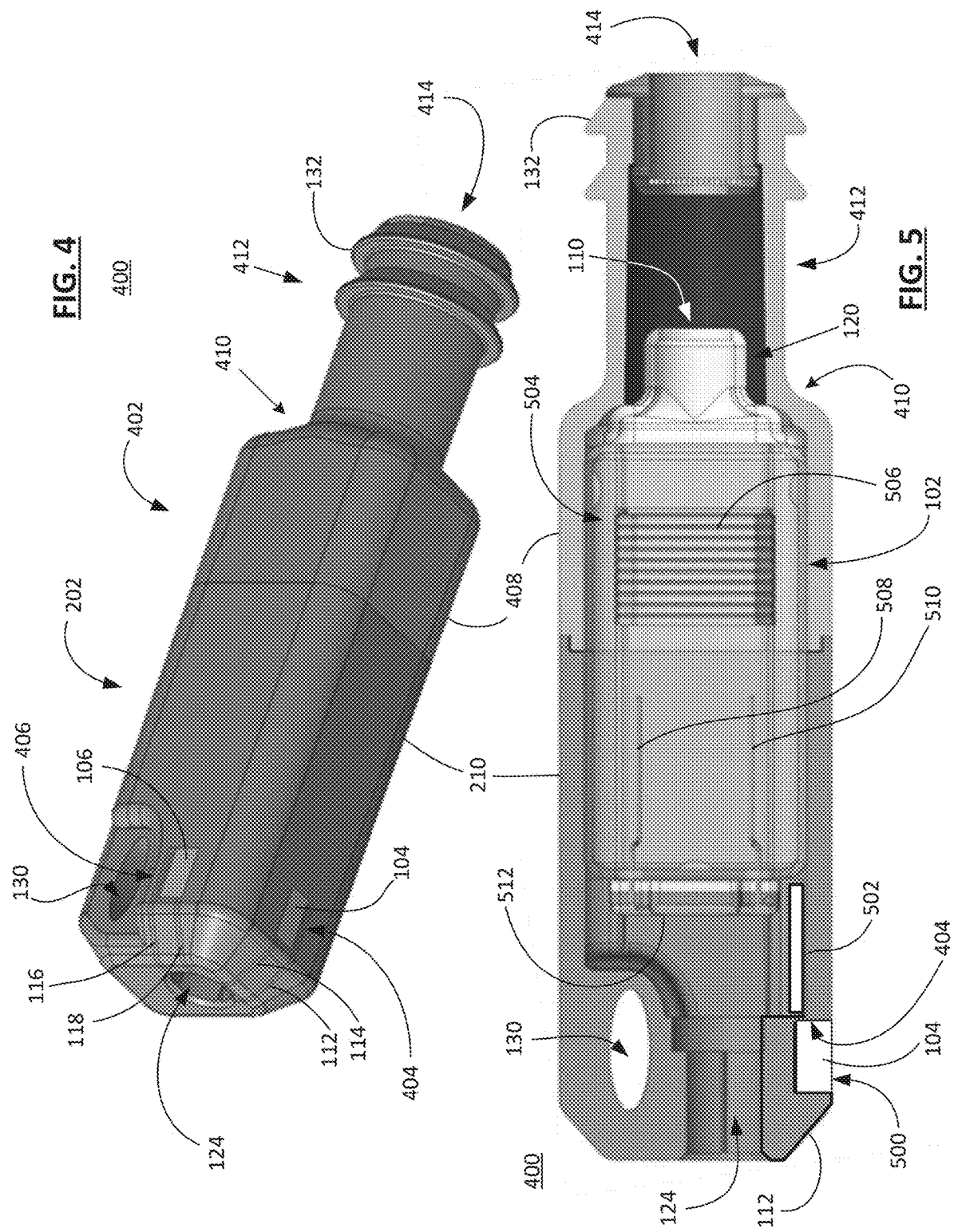

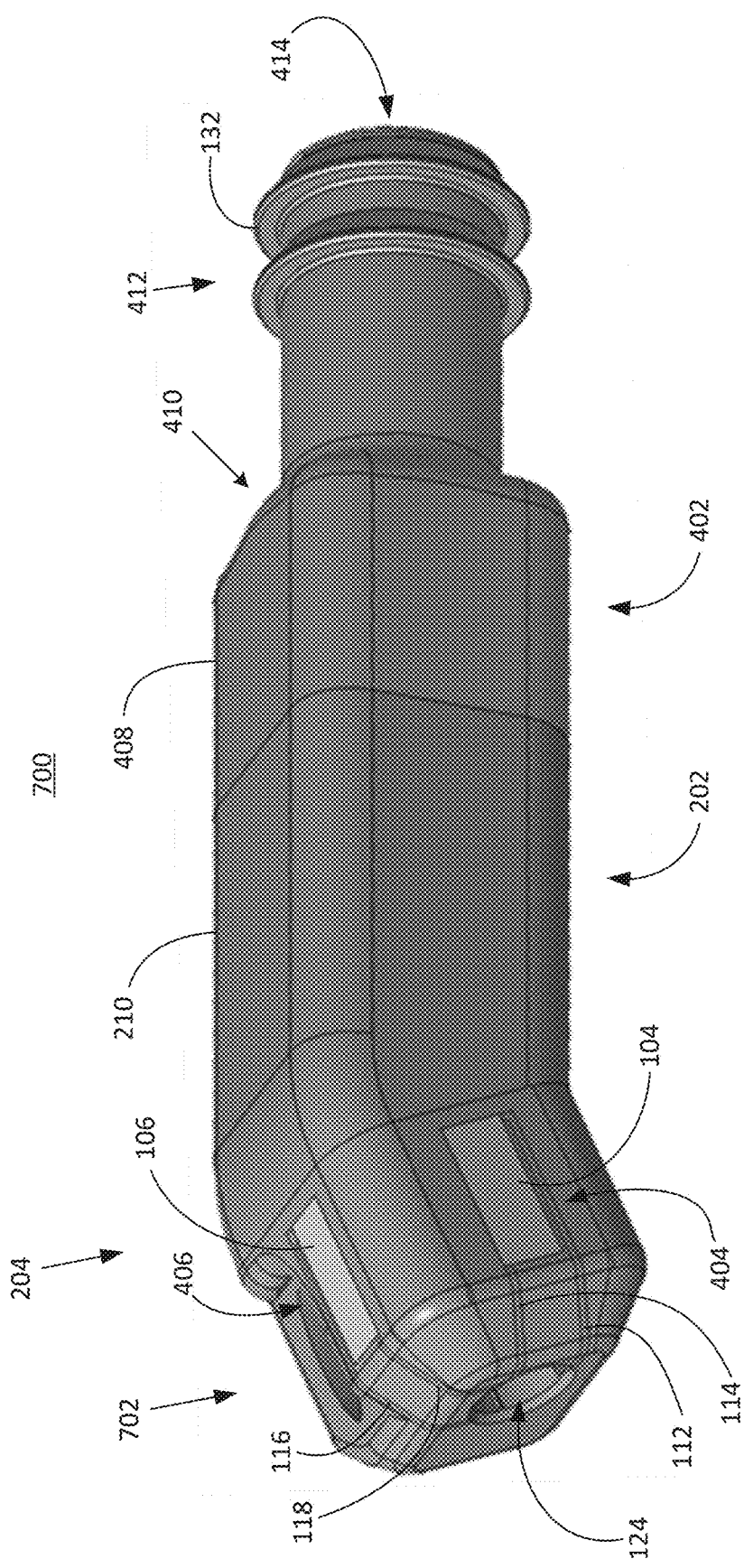

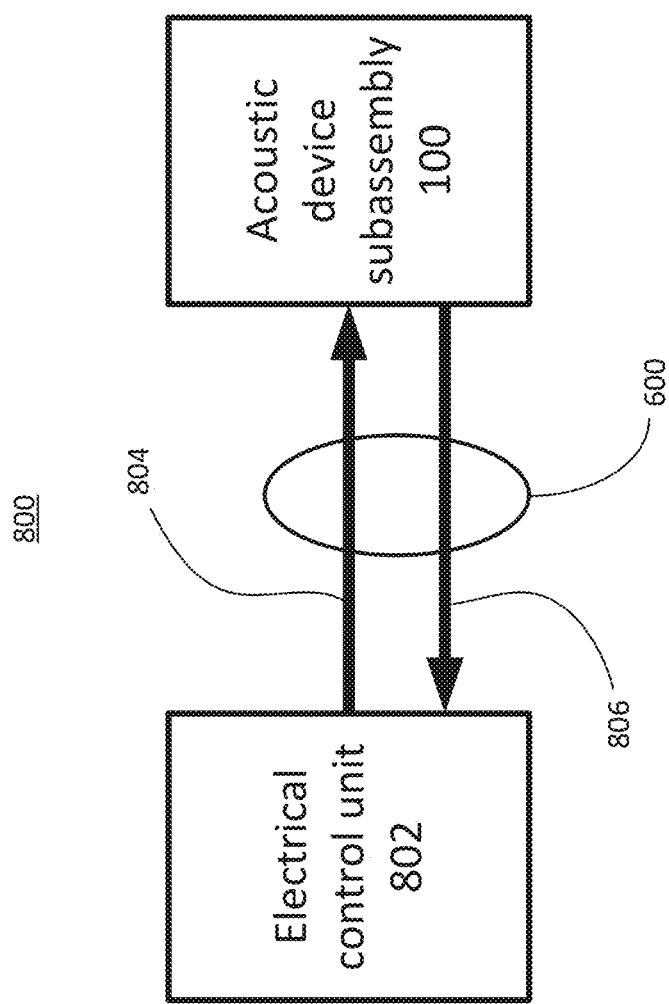

RECEIVER HOUSING WITH INTEGRATED SENSORS FOR HEARING DEVICE

RELATED APPLICATIONS

This application claims priority to U.S. Provisional Patent Application Ser. No. 62/786,992 filed on Dec. 31, 2018, entitled "Receiver Housing with Integrated Sensors for Hearing Device," the entire contents of which is hereby incorporated by reference.

TECHNICAL FIELD

This disclosure relates generally to hearing devices and, more specifically, to hearing devices including a portion that extends at least partially into a user's ear canal, a sound-producing electroacoustic transducer and one or more sensors.

BACKGROUND

Hearing devices including hearing aids and earphones among other devices having a sound-producing electroacoustic transducer, such as a balanced armature receiver, and an ear tip for insertion into a user's ear canal are known generally. A sound-producing electroacoustic transducer is also referred to herein as a receiver or speaker. Receiver-in-canal (RIC) devices among others are electrically connected to a behind-the-ear (BTE) unit by an electrical cable. Other hearing devices may be wholly contained on or in the ear. The overall size of such devices and particularly the ear-fitting portion thereof is constrained by the need to fit within the user's ear canal thus limiting the ability to integrate other components.

The objects, features and advantages of the present disclosure will become more fully apparent to those of ordinary skill in the art upon careful consideration of the following Detailed Description and the appended claims in conjunction with the drawings described below.

BRIEF DESCRIPTION OF THE DRAWINGS

FIG. 4 is a perspective view of a hearing device subassembly;

FIG. 5 is a partial sectional view of the hearing device subassembly of FIG. 4;

FIG. 7 is a perspective view of a hearing device subassembly;

FIG. 8 is a schematic diagram illustrating a hearing device incorporating the hearing device subassembly disclosed herein along with an electrical control unit.

Figure 1A:
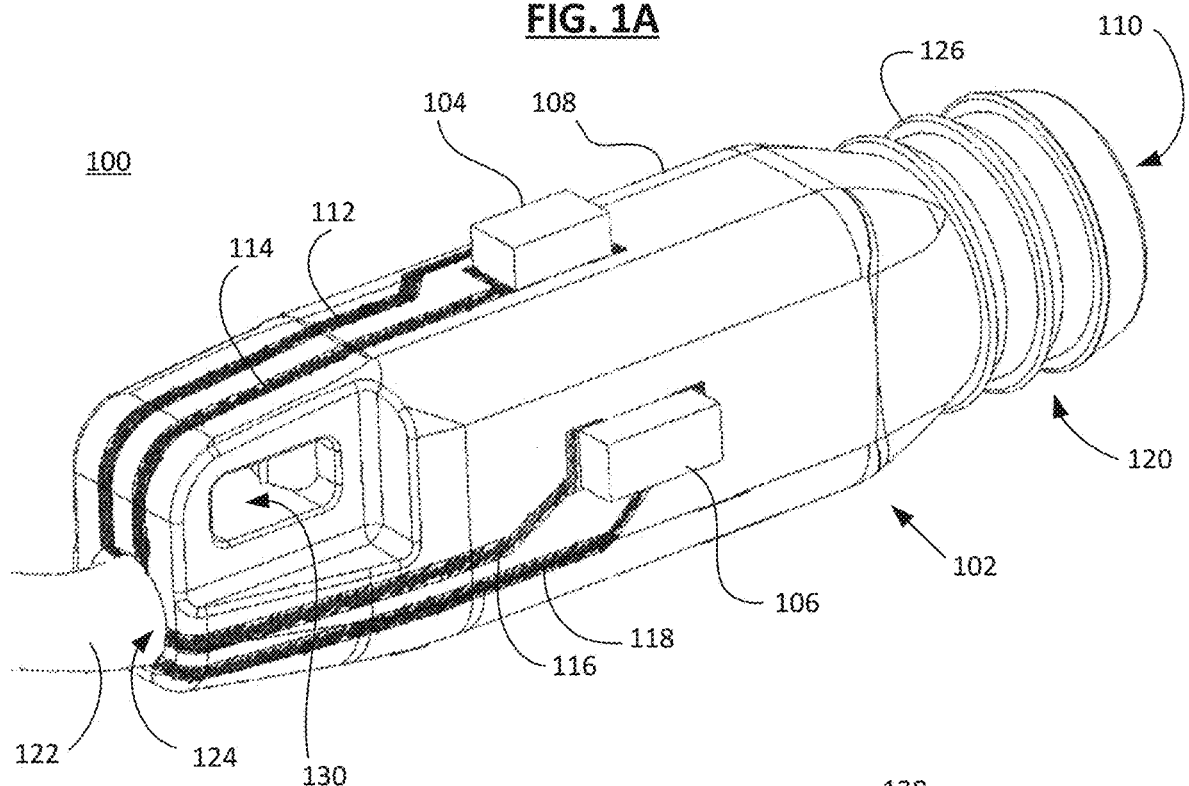
FIG. 1A is a perspective view of a hearing device subassembly.

Elements in the figures are illustrated for simplicity and clarity and have not necessarily been drawn to scale or to include all features, options or attachments. For example, the dimensions and/or relative positioning of some of the elements in the figures may be exaggerated relative to other elements to help to improve understanding of various embodiments. Also, common but well-understood elements that are useful or necessary in a commercially feasible embodiment are often not depicted in order to facilitate a less obstructed view of these various embodiments. The terms and expressions used herein have the ordinary technical meaning as is accorded to such terms and expressions by persons skilled in the technical field as set forth above except where different specific meanings have otherwise been set forth herein.

DETAILED DESCRIPTION

The disclosure relates to hearing devices and subassemblies for hearing devices. In one implementation a hearing device subassembly comprises generally a sleeve member configured for at least partial insertion into a user's ear canal. The sleeve member includes a cavity configured to receive and retain at least a portion of a sound-producing electroacoustic transducer. One or more sensors are integrated with the sleeve member and positioned to sense one or more conditions external to the sleeve member when the sleeve member is at least partially inserted into the user's ear canal. The sleeve member includes a cable interface wherein electrical contacts of the sound-producing electroacoustic transducer received in the cavity of the sleeve member are electrically accessible via the cable interface. Conductive traces integrated with the sleeve member are electrically connected to the sensor and are electrically connectable via the cable interface. In another implementation, the subassembly includes the sleeve member combined with an electrical cable. In other implementations, the sleeve member and electrical cable are combined with the sound-producing electroacoustic transducer. The foregoing subassemblies may be combined with other parts of the hearing device, for example, with a BTE unit.

In another implementation, a hearing device subassembly comprises a sleeve member configured for at least partial insertion into a user's ear canal, the sleeve member defining a cavity configured to receive and retain at least a portion of a sound-producing electroacoustic transducer and the sleeve member having a sensor attached thereto, the sensor oriented to sense a condition external to the sleeve member, and a sound-producing electroacoustic transducer including an acoustic output and an electrical interface, the sound-producing electroacoustic transducer disposed and retains in the cavity of the sleeve member. The foregoing subassemblies may be combined with other parts of the hearing device, for example, with an electrical cable or a BTE unit.

In another implementation, the hearing device comprises a sleeve member configured for at least partial insertion into a user's ear canal, a sensor integrated with the sleeve member and positioned to sense a biomarker when the sleeve member is at least partially inserted into the user's ear canal, conductive traces integrally formed with the sleeve member, one of the conductive traces electrically connected to the sensor, a sound-producing electroacoustic transducer at least partially disposed and retained in a cavity of the sleeve member, an electrical cable coupled to a cable interface of the sleeve, a conductor of the electrical cable electrically connected to one of the conductive traces and to contacts of the sound-producing electroacoustic transducer, and a nozzle acoustically coupled to an acoustic output of the sound-producing electroacoustic transducer.

Figure 2:
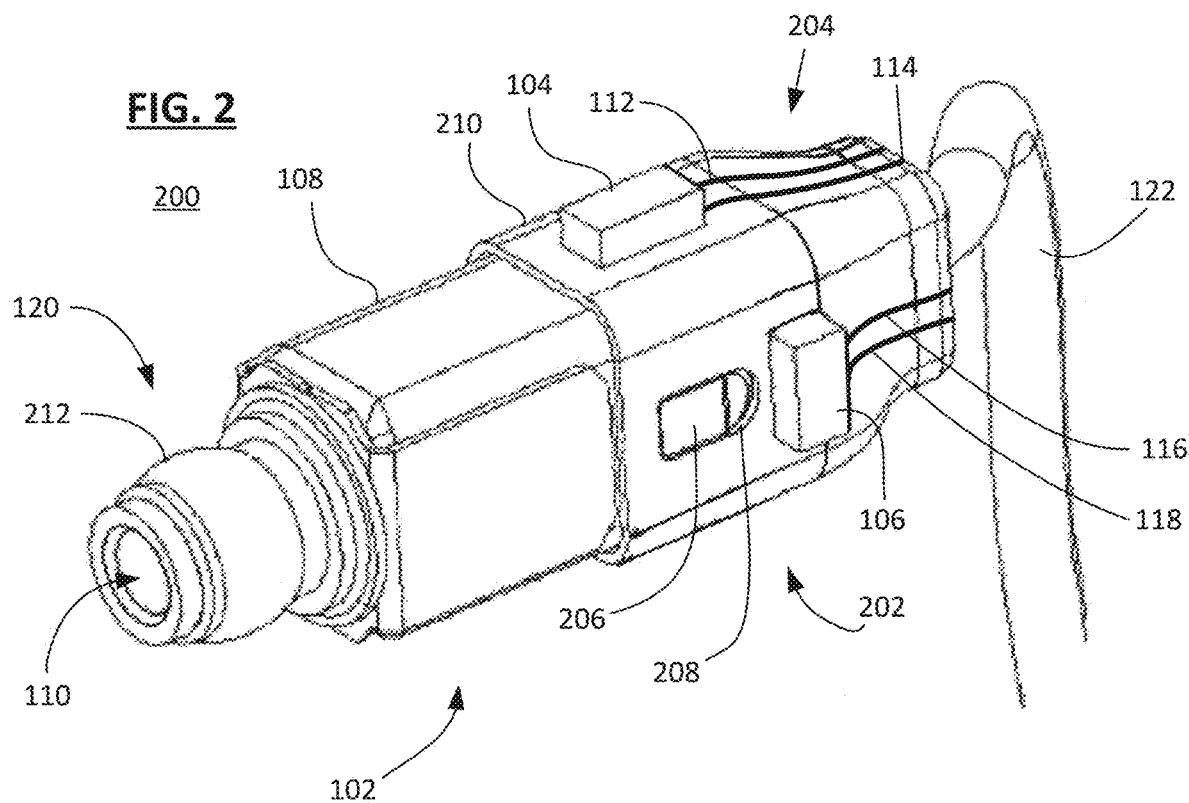
FIG. 2 is a perspective view of a hearing device subassembly.
Figure 3:
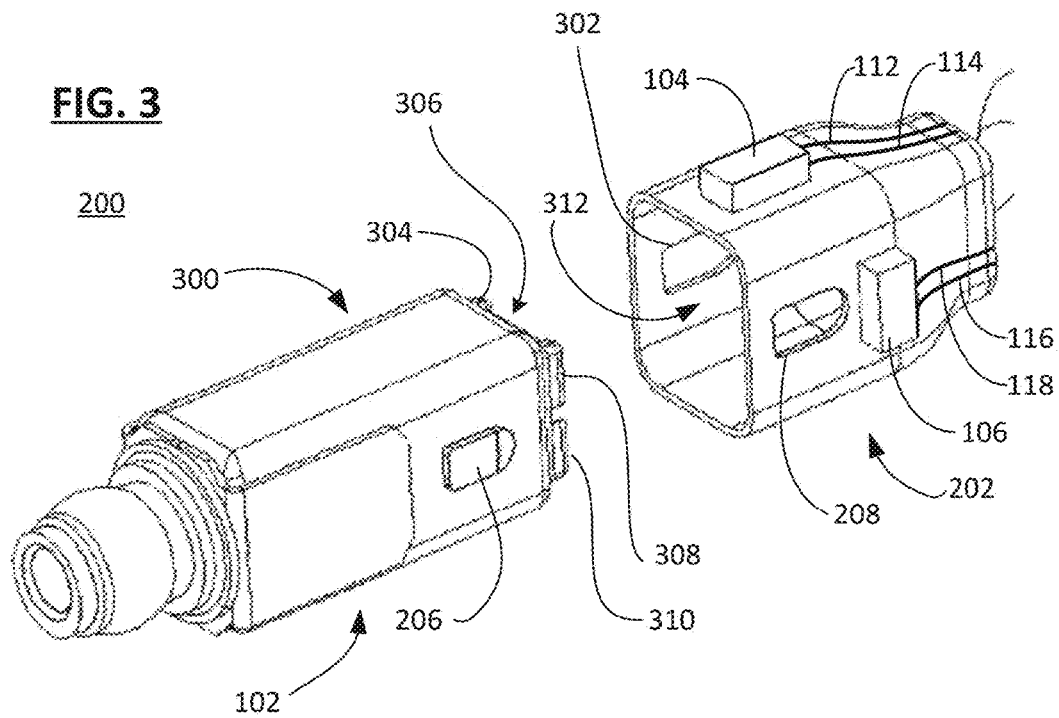
FIG. 3 is an exploded view of the hearing device subassembly of FIG. 2.

In embodiments where the transducer is only partially disposed in the sleeve member, a portion of the transducer protruding from the sleeve member includes a nozzle to which an ear tip is connectable. FIGS. 2-3 show a sleeve member 202 including a cavity, shown as 312 in FIG. 3, which includes an opening into which a receiver 102 is partially disposed and retained. In this embodiment, as shown in FIG. 1, a portion 108 of the receiver 102 protrudes from the sleeve member and includes a nozzle 120 having a sound port 110 acoustically coupled to an acoustic output of the receiver.

The receiver can be permanently or releasably retained in the sleeve member. In FIGS. 2-3, the sleeve member 202 and the receiver 102 include complementary structures to releasably retain the receiver. This structure includes a pair of retention apertures 208, 302 formed in a wall portion of the sleeve member 202 that accommodate a pair of protrusions 206, 300 having complementary shapes and sizes formed or disposed on the receiver. The sleeve member may be fabricated from plastic or some other pliable material that deforms sufficiently to permit insertion of the receiver and protrusions into the cavity until the protrusions seat in the corresponding apertures 208, 302. A sleeve member made from a pliable material may also permit ready removal of the receiver from the cavity, for service or replacement. Alternatively, the locations of the apertures and protrusions can be reversed. In other embodiments, other retention structures may be deployed. For example, the retention structure may include flexible clips, fasteners, or other fastening mechanisms that releasably connect the receiver to the sleeve member. In other embodiments, however the receiver is permanently fastened to the sleeve member by an adhesive or by permanent fasteners.

In other embodiments, the sleeve member substantially fully encapsulates the receiver, wherein the sleeve member includes a nozzle to which the ear tip is connectable. A sleeve member substantially fully encapsulating the transducer may be embodied as an assembly of two or more components. Alternatively, a unitary sleeve member substantially fully encapsulating the transducer may be formed about the transducer in an insert molding or other sleeve forming operation. In other embodiments, the unitary sleeve member is formed of a pliable material and the sound-producing electroacoustic transducer is inserted into the cavity of the sleeve member after the sleeve member is manufactured.

In FIGS. 4-7, the sleeve member 202 includes a sleeve extension member 402 that connects to the sleeve member such that the sleeve member and the sleeve extension member together form an assembly that substantially fully encapsulates the receiver. In this embodiment, the sleeve extension member 402 has a curved portion 410 forming a narrow neck with a nozzle 412 having a sound port 414. In an alternative embodiment, the assembly is formed by symmetric or asymmetric clamshell members. In the clamshell embodiments, a clamshell seam can extend through the nozzle and the cable interface. In another clamshell embodiment, a panel on the sleeve assembly provides access to the cavity. In FIGS. 4-7, a surface 408 of the sleeve extension member 402 is flush with a surface 210 of the sleeve member 202. In other embodiments however a diameter of the sleeve extension member is larger than a diameter of the sleeve member, or vice versa, to accommodate telescopic coupling of the sleeve member and the sleeve extension member.

Figure 6:
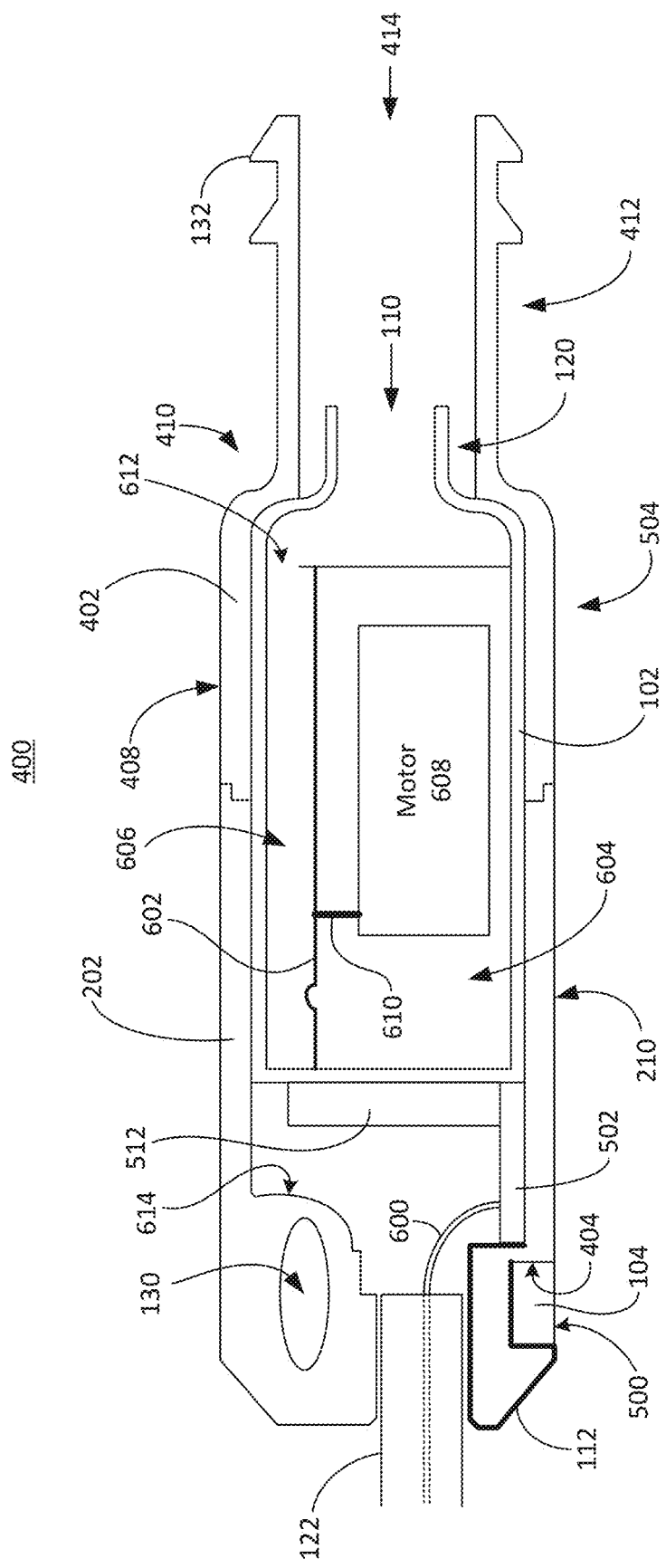
FIG. 6 is a schematic diagram of the hearing device subassembly of FIG. 4.

In embodiments wherein the sleeve member is an assembly substantially fully encapsulating the receiver, the receiver may be inserted into at least a portion of the cavity prior to assembly. When fully assembled, structure within the sleeve member assembly positions and retains the receiver so that an acoustic output 110 of the receiver is acoustically coupled to the sound port 414 of the nozzle 412, as shown in FIGS. 5 and 6. The sleeve member assembly components can be assembled permanently or can be releasably coupled to permit ready access to, or replacement of, the receiver and any wax guard located in the cavity. The sleeve member and sleeve extension member components may be welded, clipped, screwed, glued or otherwise permanently or releasably fastened.

The ear tip generally comprises a body member having an acoustic passage and an ear interface portion disposed at least partially about the body member. In one embodiment, the ear interface portion is embodied as a dome, although other structures may be used. In some embodiments, the ear tip forms a substantial acoustic seal when at least partially inserted into the user's ear canal. A substantial acoustic seal is not a perfect seal, but rather a seal that blocks a significant part of the acoustic spectrum. In other embodiments, the ear tip does not form an acoustic seal thereby permitting the passage of ambient sounds into the ear canal. An unsealed ear tip permits ambient sounds to complement amplified sound frequencies produced by the hearing device. The ear tip may be made of any material suitable for contact with users' ear canals including but not limited to foams, silicone among other known and future materials. Ear tips are well known generally by those having ordinary skill in the art and are not discussed further herein except to the extent the ear tip is coupled to the nozzle of the hearing device subassembly.

Figure 1B:
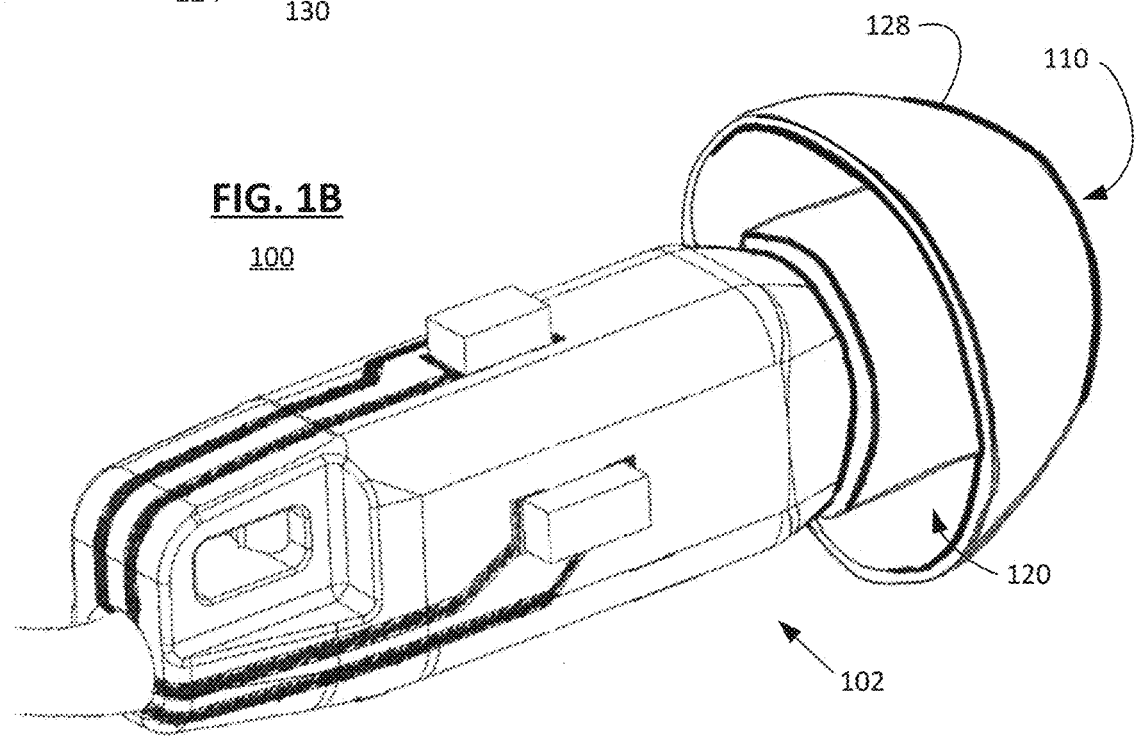
FIG. 1B is a perspective view of the hearing device subassembly of FIG. 1 including an ear tip.

FIG. 1B shows an ear tip 128 removably coupled to a ribbed nozzle on a narrow neck of the sleeve assembly, wherein a portion of the body member fits over the narrow neck. The subassembly of FIG. 1A shows the nozzle 120 with ribs 126 to which the ear tip of FIG. 1B is removably fastened. FIG. 2 shows a nozzle 120 having a bulbous structure 212 for retaining an ear tip. FIGS. 4-7 also show the sleeve member having a transition 410 forming a narrow neck with a nozzle 412 having ribs 132. Alternatively, the ear tip may be integrally formed with the sleeve member without the need to attach a separate part. Such an ear tip may be formed in a multi-shot molding operation wherein the ear tip is formed of a softer material than the sleeve member. FIGS. 1A and 4-6 also show an opening 130 in either the receiver housing or the sleeve member to accommodate a flexible member that conforms to the user's ear. Such a flexible member, also known as a concha lock or an ear feather, helps retain the device in the user's ear.

FIGS. 1A, 4, 5 and 7 show the sleeve member having a cable interface that receives and retains a connector portion of an electrical cable electrically connectable to the receiver and other electrical components integrated with the sleeve member. FIGS. 1A, 2 and 6 show an electrical cable 122 coupled to the cable interface of the sleeve member. The cable interface shown includes a socket with a recess for accommodating a flange (not shown) of the electrical cable to prevent separation of the cable from the sleeve member. FIG. 8 shows this interconnection schematically, wherein the electrical cable 804 interconnects the hearing device subassembly 100 to another device having an electrical control unit 802. The control unit may be a BTE unit or some other device to which the subassembly is electrically connected.

One or more sensors are integrated with the sleeve member and positioned to sense one or more conditions external to the sleeve member when the sleeve member is at least partially inserted into the user's ear canal. The one or more sensor may be positioned to detect conditions outside or inside the ear canal. Some sensors are positioned to detect biomarkers of the user. For example, the sensor may detect one or more of blood pressure, pulse rate, body temperature among other biomarkers of the user from within the ear canal. Such conditions may be detected by infrared (IR), light, or ultrasonic sensors, among others that are integrated with the sleeve member. A microphone sensor may detect other conditions, like sound, inside or outside the user's ear canal, for example for adaptive or active noise cancellation (ANC). Others sensors (e.g., proximity or capacitive sensors) may be used to detect whether the device is positioned on or in the use's ear. Still other sensors may detect temperature within or outside the ear canal. Other sensors (e.g., accelerometers, inertial sensors, etc.) may detect shock to the hearing device or a falling user. Combinations of these and other sensors may be integrated with the sleeve member. The positions and orientations of the one or more sensors on the sleeve member depend generally on the condition sensed and whether the condition is in the ear canal or outside of it. Some sensors may include a lens or be integrated with a discrete lens component, for example to focus light or some other signal.

In FIGS. 1A, 2, 3, 4 and 7, multiple sensors 104 and 106 are integrated with the sleeve member. In one implementation, one sensor is a signal emitter and the other sensor is a signal receiver positioned in space-apart relation on the sleeve member such that the signal receiver can receive the signal emitted by the signal emitter. Alternatively, the emitter and receiver can be co-located. More generally, sensors other than emitter/receiver sensors may also be used, examples of which are described herein.

Generally, the sleeve member includes openings on the surface thereof to receive and retain one or more sensors. The openings can be embodied as recesses on a wall portion 210 of the sleeve member or as holes extending fully through the wall portion such that the sensors are placed in the apertures and secured in place. The sensors may be disposed in corresponding openings from inside or outside the sleeve member. FIGS. 4-7 show sensors 104, 106 located in recessed portions 404, 406 of the sleeve member, respectively. Sensor obstruction may be problematic on some portions of the sleeve member, for example portions that extend deeper in the ear canal. Thus where a sensor is susceptible to wax or debris accumulation, it may be desirable for the outer surface of the sensor, including any lens associated therewith, to be flush or at least not protrude substantially beyond the outer surface of the sleeve member. Flush and protruding sensors may be readily cleared or wipes clean of accumulation and debris, whereas sensors with recessed outer surfaces may more difficult to clear of obstruction. In FIG. 6, the recessed portions are sized and shaped so that an outer surface 500 of each sensor is substantially flush with the surface 210 of the sleeve member. Depending on location, the extent to which a sensor protrudes from the sleeve member may or may not be problematic. Minor protrusions may be acceptable on most parts of the sleeve member whereas more substantial protrusions may adversely affect the fit of the sleeve member in the ear canal. Sensors with recessed outer surfaces may not be problematic where the sensors are located away sources of wax or debris, for example, farther away from the ear canal.

In some embodiments, the sleeve member includes a sloped or curved portion to facilitate proper insertion into the ear canal and to improve overall fit and comfort. FIG. 7 shows the sleeve member 202 of the hearing device subassembly 700 including a sloped portion 702 extending from the curved portion 204 of the sleeve member 202. The sloped portion 702 may reduce protrusion of the sleeve member from within the ear canal or reduce discomfort associated with the sleeve member in embodiments where the sleeve member has a relatively long dimension. In some embodiments, the sleeve member is made from a non-ferromagnetic metal, for example an austenitic stainless steel, plastic, or carbon fiber. Other suitable materials can also be employed to form the sleeve member.

The hearing device or subassembly generally includes one or more conductive traces integrally formed with the sleeve member such that one or more conductive traces are electrically connected to each sensor. FIGS. 1-3 show conductive traces 112, 114 and 116, 118 extending from the sensors 104, 106, respectively, along the surface of the sleeve member. FIGS. 4-7 show the conductive traces 112, 114 extending from within the recessed portion 404 to the sensor 104, and conductive traces 116, 118 extend from within the recessed portion 406 to sensor 106. In FIGS. 5 and 6, the trace 112 extends from the recessed portion 404 toward the surface 210, along a surface of the cable interface 124 and into an inner surface 614 of the sleeve member where the trace 112 connects to a contact 502. The contact 502 is a conductive material that electrically couples the sensor with a conductor 600 located within the electrical cable 122. The trace 112 may be connected to the cable contact 502 via welding, soldering, or other suitable means known in the art. In some embodiments, instead of extending along a surface of the sleeve member, the traces can be coupled to a conductive via extending through an opening or aperture formed in the sleeve member. The conductive via may be electrically coupled to a contact 502 within the sleeve member.

In some embodiments, the conductive traces are formed on the surface of the sleeve member via laser direct structuring (LDS), metal deposition, insert-molding or other fabrication process. For example, in the LDS process, a sleeve member made of a thermoplastic material including a metallic inorganic compound that can be activated using a laser to form the conductive traces in a well-known process. In some embodiments, the surface onto which the traces are to be placed has a plurality of preformed grooves into which the traces are subsequently embedded to eliminate or reduce protrusions on the outer surface of the sleeve member. In some embodiments, the traces are placed on the surface via laser metal deposition (LMD). In other embodiments, conductive ink may be used to form the traces on the surface. Other methods of forming and attaching such traces can be employed as suitable.

The hearing device or subassembly generally includes a sound-producing electroacoustic transducer. In one embodiment, the sound-producing electroacoustic transducer is a balanced armature receiver. In FIGS. 5-6, a balanced armature receiver 504 is disposed in the receiver retention cavity. In FIG. 6, the balanced armature receiver 504 includes a housing and a diaphragm 602 driven by a motor 608. The diaphragm 602 separates the housing into a back volume 604 and a front volume 606 having an acoustic output 612. The motor is disposed in the back volume and includes a coil magnetically coupled to an armature balanced between two magnets. The armature is mechanically coupled to the diaphragm by a link 610 and the two vibrate in tandem in response to an excitation signal applied to the coil as is known generally. In other embodiments, the sound-producing electroacoustic transducer is a dynamic speaker having a conventional motor and diaphragm as is known generally. In other embodiments, other known or future sound-producing electroacoustic device may be used alternatively.

In FIG. 5, the receiver 504 includes an electrical interface 512 having one or more contacts electrically connectable to the electrical cable when the receiver is received in the cavity of the sleeve member. For example, the electrical cable can be attached to the sleeve member before the receiver is disposed in the cavity. The cable interface of the sleeve member may include contacts to which contacts of the receiver interface are electrically connected, e.g., by friction contact, when the receiver is disposed in the cavity. In other embodiments, like the clamshell designs described herein, one or more conductors of the electrical cable can be soldered to corresponding contacts of the electrical interface before the cable and receiver are inserted into the cavity. FIG. 3 shows the receiver having an electrical interface 306 with multiple contacts 304, 308 and 310. FIG. 5 shows an electrical interface 512 with contacts embodied as a single terminal board fixed to an end of the receiver housing and electrically coupled to coil leads 508, 510. Conductors of the electrical cable can likewise be electrically connected to corresponding contacts of the sleeve member when the cable is inserted into the cable interface from outside the sleeve member. Contacts can be insert molded in the sleeve member or formed using laser direct structuring (LDS) or by other means. Other suitable processes for forming the contacts and connecting the contacts to the receiver conductors of the electrical cable and conductive traces may be used alternatively.

FIG. 8 shows the hearing device subassembly 100 connected to an electrical control unit 802 via the electrical conductors 600, e.g. wires, within a hearing device 800. The control unit sends one or more electrical excitation signal 804 to the sound-producing electroacoustic transducer within the subassembly 100, and in turn the subassembly sends one or more sensor output signal 806 obtained using the sensors implemented therein back to the control unit. Other types of signals can also be transmitted between the subassembly and the control unit. Also, it should be noted that any hearing device subassembly as disclosed herein can be used in lieu of the subassembly in the hearing device, as appropriate. In one embodiment, the control unit is part of the in-canal portion of the hearing device. The control unit 802 can be located in a behind the ear (BTE) unit, a necklace, headband, or in a host device like a cellphone, PC, tablet or other device located remotely from the hearing device 800. The electrical control unit 802 can be any suitable data processing unit which processes sensor output signal 806 to make decisions regarding the excitation signal 804 that it will then send back to the subassembly. In one embodiment, the electrical control unit can be connected wirelessly to the hearing device. In other embodiments the control unit is electrically connected to the receiver by an electrical cable.

While the present disclosure and what is presently considered to be the best mode thereof has been described in a manner that establishes possession by the inventors and that enables those of ordinary skill in the art to make and use the same, it will be understood and appreciated that in light of the description and drawings there are many equivalents to the exemplary embodiments disclosed herein and that myriad modifications and variations may be made thereto without departing from the scope and spirit of the disclosure, which is to be limited not by the exemplary embodiments but by the appended claimed subject matter and its equivalents.

The invention claimed is:

1. A hearing device subassembly comprising:
a sleeve member configured for at least partial insertion into a user's ear canal, the sleeve member defining a cavity configured to receive and retain at least a portion of a sound-producing electroacoustic transducer protruding from the sleeve member,
the sleeve member including a cavity into which a sound-producing electroacoustic transducer may be disposed, the sleeve member including transducer retention structure configured to retain a sound-producing electroacoustic transducer in the cavity and permit non-destructive removal of the sound-producing electroacoustic transducer from the cavity;
a cable interface on the sleeve member;
a sensor integrated with the sleeve member and positioned to sense a biomarker external to the sleeve member when the sleeve member is at least partially inserted into the user's ear canal; and
conductive traces integrated with the sleeve member, at least one of the conductive traces electrically connected to the sensor and electrically connectable via the cable interface.

2. The subassembly of claim 1 further comprising a sound-producing electroacoustic transducer at least partially disposed and retained in the cavity of the sleeve member, wherein first electrical contacts of the sound-producing electroacoustic transducer received in the cavity of the sleeve member are electrically accessible via the cable interface.

3. The subassembly of claim 1, wherein the sensor is at least partially disposed in an opening of the sleeve member.

4. The subassembly of claim 3, wherein the sensor, including any lens associated with the sensor, is not recessed below the outer surface of the sleeve member and the sensor does not protrude substantially beyond the outer surface of the sleeve member.

5. The subassembly of claim 3, wherein the sensor comprises a signal emitter and a signal receiver positioned in spaced apart relation on the sleeve member.

6. The subassembly of claim 1, the transducer retention structure including a recess in a wall portion of the sleeve member into which complementary structure on the sound-producing electroacoustic transducer is disposed and removably retained when the sound-producing electroacoustic transducer is received in the cavity of the sleeve member.

7. The subassembly of claim 1 further comprising:
a sound-producing electroacoustic transducer having a housing partially disposed and retained in the cavity of the sleeve member, the sound-producing electroacoustic transducer is a balanced armature receiver including a diaphragm separating the housing into a back volume and a front volume, the receiver including a motor disposed in the back volume, the motor having an armature coupled to the diaphragm, an acoustic output acoustically coupled to the front volume and to a nozzle of the housings; and
an electrical cable coupled to the cable interface, the electrical cable including conductors electrically connected to first contacts of the sound-producing electroacoustic transducer and to the conductive traces,
wherein the nozzle protrudes from the sleeve member.

8. The subassembly of claim 1 further comprising:
a balanced armature receiver having a housing substantially disposed and retained in the cavity of the sleeve member, the receiver including a diaphragm separating the housing into a back volume and a front volume, the receiver including a motor disposed in the back volume, the motor having an armature coupled to the diaphragm, and an acoustic output acoustically coupled to the front volume; and an electrical cable coupled to the cable interface, the electrical cable including conductors electrically connected to first contacts of the receiver and to the conductive traces, wherein the sleeve member includes a nozzle having a sound port acoustically coupled to the acoustic output.

9. The subassembly of claim 8, wherein the sleeve member is coupled to a sleeve extension member as an assembly of at least two parts and wherein the sleeve member and the sleeve extension member fully encapsulate the housing of the balanced armature receiver.

10. The subassembly of claim 1 further comprising an electrical cable coupled to the cable interface, the cable interface including second contacts electrically connected to the conductive traces and to conductors of the electrical cable, at least some of the second contacts electrically connectable to contacts of a sound-producing electroacoustic transducer when the sound-producing electroacoustic transducer is received in the cavity of the sleeve member.

11. The subassembly of claim 1, wherein the conductive traces are at least partially located on a surface of the sleeve member.

12. The subassembly of claim 1 further comprising a sound-producing electroacoustic transducer disposed and retained in the cavity of the sleeve member.

13. A hearing device subassembly comprising:

a sleeve member configured for at least partial insertion into a user's ear canal, the sleeve member defining a cavity configured to receive and retain at least a portion of a sound-producing electroacoustic transducer protruding from the sleeve member, the sleeve member having a sensor attached thereto and conductive traces, the sensor including an emitter portion and a receiver portion located on different surfaces of the sleeve member to sense a condition external to the sleeve member; and a sound-producing electroacoustic transducer including an acoustic output and an electrical interface, the sound-producing electroacoustic transducer disposed and retained in the cavity of the sleeve member.

14. The subassembly of claim 13, wherein the sensor is at least partially located in an opening of a wall portion of the sleeve member such that an outermost surface of the sensor is not recessed below the outer surface of the sleeve member and the outermost portion of the sensor does not protrude substantially beyond the outer surface of the sleeve member.

15. The subassembly of claim 13, the sleeve member further comprising a cable interface, the conductive traces and contacts of the sound-producing electroacoustic transducer electrically connectable to conductors of an electrical cable via the cable interface.

16. The subassembly of claim 15, the sound-producing electroacoustic transducer and the sleeve member comprising complementary retention portions that engage each other when at least the portion of the sound-producing electroacoustic transducer is disposed in the cavity of the sleeve member, wherein the retention structure releasably retains the sound-producing electroacoustic transducer in the cavity of the sleeve member.

17. The subassembly of claim 13, wherein the sensor is a biosensor located on the sleeve member to sense a biomarker when the sleeve member is at least partially inserted into the user's ear canal.

18. A hearing device comprising:

a sleeve member configured for at least partial insertion into a user's ear canal, the sleeve member having a cavity into which a sound-producing electroacoustic transducer may be disposed, retention structure configured to retain a sound-producing electroacoustic transducer in the cavity to protrude from the sleeve member and to permit non-destructive release of the sound-producing electroacoustic transducer from the cavity, and a cable interface;

a sensor integrated with the sleeve member, the sensor positioned to sense a biomarker when the sleeve member is at least partially inserted into the user's ear canal;

conductive traces disposed on an outer surface of the sleeve member and integrally formed with the sleeve member, at least one of the conductive traces electrically connected to the sensor;

a sound-producing balanced armature receiver including a housing having a diaphragm separating the housing into a back volume and a front volume having an acoustic output, the balanced armature receiver including a motor disposed in the back volume, the motor having an armature coupled to the diaphragm, the housing of the balanced armature receiver at least partially disposed and retained in the cavity of the sleeve member;

an electrical cable coupled to the cable interface of the sleeve member, conductors of the electrical cable electrically connected to the conductive traces and to contacts of the balanced armature receiver; and a nozzle acoustically coupled to the acoustic output of the balanced armature receiver.

19. The hearing device of claim 18, wherein the sensor, including any lens associated with the sensor, is not recessed below the outer surface of the sleeve member and the sensor does not protrude substantially beyond the outer surface of the sleeve member.

* * * * *